United States Patent [19]

Kos et al.

[11] Patent Number: 5,475,141
[45] Date of Patent: Dec. 12, 1995

[54] PROCESS FOR PREPARING PRIMARY AMINES FROM ALDEHYDES

[75] Inventors: Carlo Kos, Leonding; Friedrich Hebesberger, Wilhering; Eduard Artner, Linz; Engelbert Kloimstein, Eferding; Robert Haar, Engerwitzdorf; Ernst Lust, Linz, all of Austria

[73] Assignee: Chemie Linz GmbH, Linz, Austria

[21] Appl. No.: 253,305

[22] Filed: Jun. 3, 1994

[30] Foreign Application Priority Data

Jun. 7, 1993 [AT] Austria ................... 1100/93

[51] Int. Cl.⁶ ................................................. C07C 209/00
[52] U.S. Cl. ..................... 564/473; 564/469; 564/472
[58] Field of Search ........................... 564/472, 473, 564/469; 546/314

[56] References Cited

U.S. PATENT DOCUMENTS

| | | | |
|---|---|---|---|
| 2,657,240 | 10/1953 | Foster et al. | 564/423 |
| 4,054,588 | 10/1977 | Siclari et al. | 564/473 |
| 4,197,260 | 4/1980 | Siclari et al. | 564/473 |
| 4,206,149 | 6/1980 | Slaugh | 564/473 |
| 4,218,399 | 8/1980 | Siclari et al. | 562/553 |
| 4,229,374 | 10/1980 | Slaugh et al. | 564/473 |
| 4,329,297 | 5/1982 | Rossi et al. | 562/553 |
| 4,400,533 | 8/1983 | aus der Funten et al. | 562/443 |
| 4,766,237 | 8/1988 | Hutmacher et al. | 560/155 |
| 4,950,429 | 8/1990 | Vagt et al. | 562/553 |
| 5,055,618 | 10/1991 | Kampmann et al. | 564/473 |

FOREIGN PATENT DOCUMENTS

| | | |
|---|---|---|
| 1273365 | 11/1959 | France . |
| 824492 | 12/1951 | Germany . |
| 2314697 | 3/1973 | Germany . |
| 2149790 | 6/1985 | United Kingdom . |

OTHER PUBLICATIONS

E. R. Alexander et al., J. Am. Chem. Soc. 70 (1948) pp. 1315–1316.

Pollart and Miller, J. Org. Chem. 27, (1962), pp. 2392–2394.

White et al., Tetrahedron Letters No. 39, (1971), pp. 3591–3593.

Diaper and Mitchel, Canadian Journal of Chemistry, vol. 40 (1962), pp. 1189–1195.

Houben Weyl, Methoden der organischen Chemie, Band XI/1, 1957, p. 604.

Chem. Abst., vol. 116: 020679v (1992).

Chem. Abstr. vol. 82: 003768k (1975).

Metayer et al., Bull. Soc. Chim., France, 1954, pp. 615–621.

Primary Examiner—Werren B. Lone
Attorney, Agent, or Firm—Wenderoth, Lind & Ponack

[57] ABSTRACT

Process for preparing primary amines from aldehydes by mixing an aldehyde with a diluent, where in the case of an alcohol or of water as diluent the mixing temperature is at most 5° C. to prevent the formation of the hemiacetal or the aldehyde hydrate, and bringing the mixture into contact with a mixture of ammonia, hydrogen and hydrogenation catalyst, whereby the formation of an imine is prevented, at temperatures of from 60° to 180° C. and pressures of from 20 to 60 bar, at least 15 mol of ammonia being used per mol of aldehyde group, and also an apparatus for carrying out the process.

9 Claims, 1 Drawing Sheet

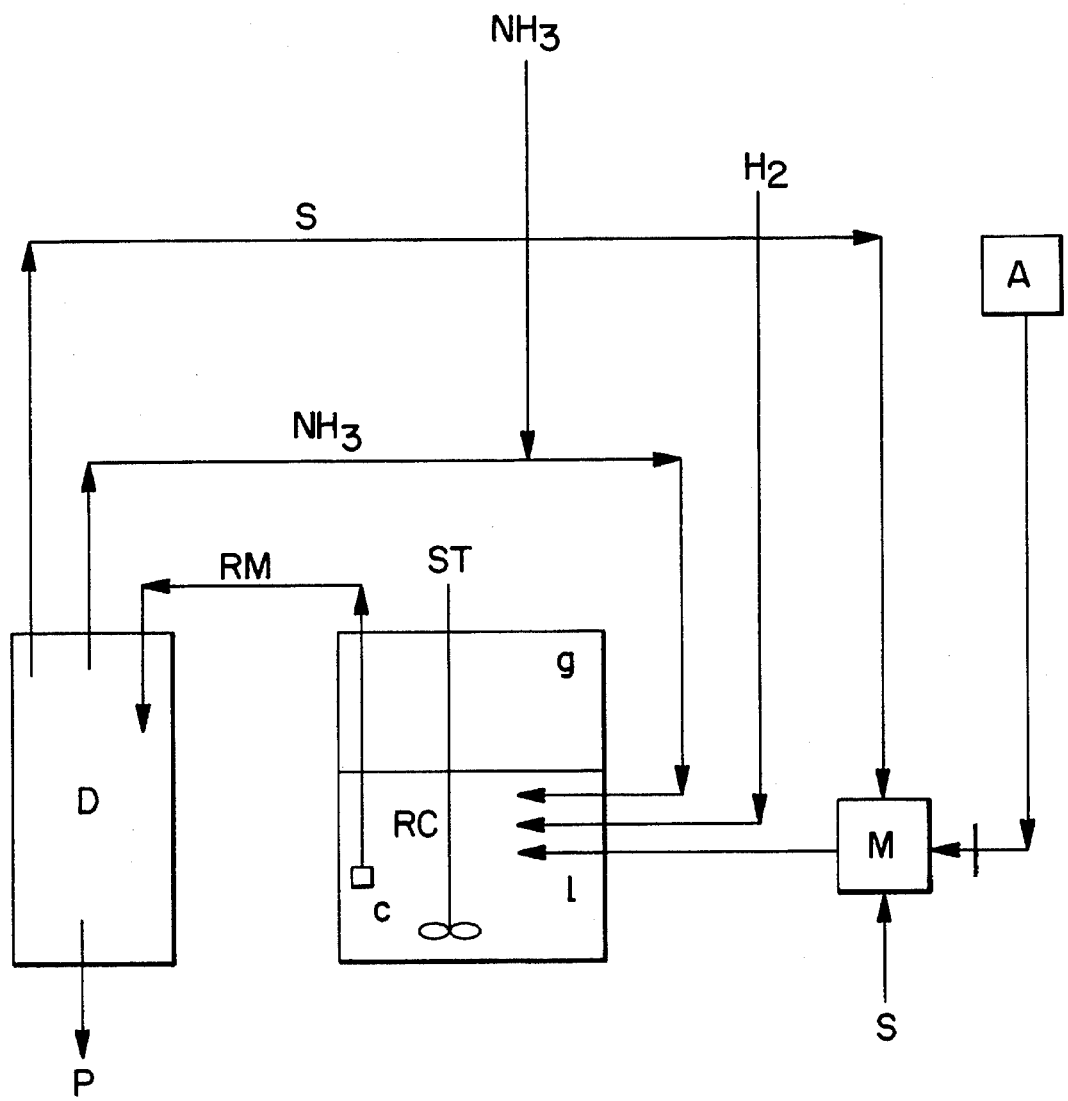

PROCESS FOR PREPARING PRIMARY AMINES FROM ALDEHYDES

Primary amines and diamines, such as for example hexamethylenediamine are important building blocks in the synthesis of organic compounds. They can be prepared, for example, by reductive amination of aldehydes or of other products derived from the ozonolysis of olefinic double bonds. Although the reductive amination of carbonyl compounds has been known for some time, no process could hitherto be found in which the formation of secondary and tertiary amines could be prevented and in which the primary amines are obtained after a short reaction time in pure form and in high yields.

Thus, J. Am. Chem. Soc. 70 (1948), pp. 1315–1316 describes the reductive alkylation of ammonia with ketones and aldehydes in the presence of ammonium chloride, absolute ammonia-saturated methanol, hydrogen and platinum oxide as catalyst, the yields being from 10 to at most 69%.

U.S. Pat. No. 2,657,240 discloses the ozonization of cyclohexene in a saturated aliphatic alcohol and the treatment of the ozonolysis product with an excess of ammonia in the presence of a hydrogenation catalyst and subsequently or simultaneously with hydrogen to form hexamethylenediamine, although only in low yields and after a long reaction time.

The reaction of olefinic double bonds with ozone and reaction of the ozonolysis product with ammonia and hydrogen in the presence of a hydrogenation catalyst to prepare amines is also described in Pollart and Miller, J. Org. Chem. 27, (1962), pp. 2392–94. However, the degree of conversion of the various olefins is only from 12.5 to at most 71%. According to White et al., Tetrahedron Letters No. 39, (1971), pp. 3591–3593, an improvement of this method is said to be achieved by means of a three-stage method, namely a) ozonolysis of an olefin in an alcohol, b) catalytic hydrogenation of the ozonolysis products, c) reductive amination using a rhodium catalyst at temperatures of from 50° to 60° C. or a Raney nickel catalyst at from 80° to 100° C. However, in this case too, the yields are at most 80%.

Diaper and Mitchell, Canadian Journal of Chemistry, Vol. 40 (1962), pp. 1189–1195, describe the reductive amination of ozonolysis products of alkenols, alkenecarboxylic esters, alkenecarboxylic acid and alkeneamides to form aminoalkanols, aminoalkanecarboxylic esters, aminoalkanecarboxylic acids and aminoalkaneamides. However, here too, the yields leave something to be desired and the reaction times are long.

DE-C 824 492 discloses a process for preparing aliphatic diamines having a long chain by introducing the corresponding dialdehydes into a reaction mixture comprising ammonia, a hydrogenation catalyst and hydrogen at high pressures. According to the description, no diluent should be used if possible. According to the examples, however, water is used as diluent for the dialdehyde employed. However, in this type of reaction procedure the reaction proceeds only slowly and with formation of byproducts.

Houben Weyl, Methoden der organischen Chemie, Volume XI, 1, 1957, page 604 describes the preparation of propylamine by introducing propionaldehyde into a mixture of methanol, Raney nickel, liquid ammonia and hydrogen at a temperature of 138° C. and raising the reaction temperature while maintaining a pressure of from 40 to 140 atm by replacing the hydrogen consumed. However, this forms relatively high amounts of byproducts.

DE 26 47 317 discloses a two-stage process for preparing saturated or unsaturated, aliphatic, linear alpha, omega-diamines by reductive amination of the corresponding alpha, omega-dialdehydes, the aldehydes being reduced by the addition of ammonia in a first stage to give the diimines and these being then reduced by means of hydrogen and a catalyst to give the diamines. Although the yields according to this process are up to 90%, a two-stage method of operation means an enormous increase in apparatus required in a process carried out industrially. EP-A-0 400 426 likewise describes a two-stage process for converting an alpha, omega-dialdehyde into the corresponding primary alpha, omega-diamines, in which the dialdehyde is reacted in a first stage with a primary amine, for example butylamine, and the reaction product is reacted in a second stage in the presence of ammonia, hydrogen and a hydrogenation catalyst. Apart from the two-stage process method, this process has the additional disadvantage that the primary amine has first to be provided and later has to be removed again from the reaction mixture.

FR 2,656,864 describes a two-stage process for preparing aliphatic diamines from the corresponding dialdehydes, in which, in the first stage, the dialdehyde is reacted with an alcohol under conditions which form the di-hemiacetal which, in a second stage, is subjected to an amination and hydrogenation reaction by means of treatment with ammonia, hydrogen and a hydrogenation catalyst. The selectivity of the reaction is supposed to be 89%, but the described yield of diaminooctane starting from octanedial is actually only 52%. In addition, the processes described which have a somewhat better yield are limited to the preparation of diamines.

It has now unexpectedly been found that both monoaldehydes and organic compounds having more than one aldehyde group can be reductively aminated in a single stage and in very high yields of very pure product, the reaction times being amazingly short, by combining an aldehyde and a diluent, where in the case of an alcohol or of water as diluent the mixture is combined at sufficiently low temperatures for no hemi- or semiacetal or no aldehyde hydrate to be formed in the mixture, and by bringing the mixture directly after mixing practically simultaneously into contact with ammonia, a hydrogenation catalyst and hydrogen, whereby the formation of an imine is prevented so that the ammonia and the hydrogen come into contact directly with the aldehyde group and not with a derivative thereof.

The invention accordingly provides a process for preparing primary amines from aldehydes in the presence of a diluent, ammonia, using at least 15 mol of ammonia per mol of aldehyde group, a hydrogenation catalyst, hydrogen and isolating the amine formed from the reaction mixture, which is characterized in that an aldehyde is mixed with a diluent, where in the case of an alcohol or of water as diluent the mixing temperature is at most 5° C., so that no hemiacetal or aldehyde hydrate is formed and practically simultaneously directly afterwards the mixture is brought into contact with ammonia, hydrogen and the hydrogenation catalyst at temperatures of from 60° to 180° C. and pressures of from 20 to 60 bar.

To carry out the process of the invention, an aldehyde is dissolved in a diluent.

For the purposes of the present invention, aldehydes are aliphatic or aromatic monoaldehydes and aliphatic compounds having more than one aldehyde group, in particular dialdehydes. Aliphatic aldehydes mean saturated or unsaturated, straight-chain, branched or cyclic alkanes, alkenes or alkynes which can be substituted either only by one or a plurality of aldehyde groups and additionally by groups which are inert under the reaction conditions, such as for example phenyl, alcohol, alkoxy, amino, carboxylic acid, carboxylic ester and carboxamide groups. The phenyl group can in turn be substituted by alkyl groups or by abovementioned functional groups. Aromatic monoaldehydes are phenyl, naphthyl groups or heteroaromatic rings such as pyrrole, furan, thiophene or pyridine rings in which one of the hydrogen atoms on one of the carbon atoms is replaced by an aldehyde group and which may be unsubstituted or substituted by groups which are inert under the reaction conditions, such as for example by alkyl groups and/or abovementioned groups. Aliphatic aldehydes are preferably alkanals, alkenals, alkanedials or alkenedials having from 4 to 22 carbon atoms which may be unsubstituted or substituted by alcohol, alkoxy, amino, carboxylic acid or carboxylic ester groups and which are preferably straight-chain. Preferred aromatic aldehydes are benzaldehydes which may be unsubstituted or substituted by alkyl, alkoxy, alcohol, amino, carboxylic acid or carboxylic ester groups. Preferred heteroaromatic aldehydes are pyrrole- or pyridinealdehydes. Preferred alkyl and alkoxy groups possess from 1 to 6, particularly preferably 1–3, carbon atoms. Amino groups are unsubstituted or substituted by alkyl or phenyl groups.

Diluents which can be used are diluents which are inert under the reaction conditions, for example aliphatic hydrocarbons such as hexane, pentane, aromatic hydrocarbons such as toluene, xylenes, ethers such as isopropyl ether, methyl tert.-butyl ether, pyridine, water and alcohols or mixtures of such diluents. Preference is given to using an alcohol, toluene, methyl tert.-butyl ether, tetrahydrofuran, dioxane, pyridine, water, particularly preferably an aliphatic alcohol having from 1 to 8 carbon atoms, for example methanol, ethanol, isopropanol, hexanol, octanol, with alcohols having from 1 to 3 carbon atoms being very particularly preferred. The diluent is used in an excess over the aldehyde, preferably in a from 5- to 30-fold excess based on the weight of the aldehyde. The aldehyde used has to be soluble in the diluent.

Unexpectedly, it has been found that it is of great importance to yields, purity and reaction time in the reductive amination of aldehydes use a diluent and that the ammonia and the hydrogen react with the aldehyde group itself and not with the hemiacetal which normally forms on contact of an aldehyde with an alcohol, or with the aldehyde hydrate which normally forms on contact of an aldehyde with water, or with the imine which normally forms on contact of an aldehyde with ammonia without hydrogen and hydrogenation catalyst. It has been found that the formation of the hemiacetal or the aldehyde hydrate is prevented at mixing temperatures of aldehyde and alcohol and/or water of below 5° C., where in the case of water the freezing point is generally increased by the mixing with the aldehyde. The freezing point of the water can also be increased by addition of a second, organic, water-miscible diluent. After mixing, the mixture is brought as quickly as possible and practically simultaneously into contact with the ammonia, the hydrogenation catalyst and the hydrogen, whereby the formation of the imine is prevented.

As is customary, ammonia, hydrogen and hydrogenation catalyst are either added to the mixture of aldehyde and diluent or the mixture of aldehyde and diluent is introduced into a mixture of the ammonia with the hydrogen, optionally the diluent and the hydrogenation catalyst.

Preferably ammonia is mixed with the hydrogenation catalyst and hydrogen and optionally with the diluent. The mixture of aldehyde and diluent is introduced into this mixture which is heated to temperatures of from 60° to 200° C., preferably to from 80° to 130° C. The reaction here proceeds under pressure, with pressures of from 20 to 60 bar, preferably from 40 to 60 bar, being used. The pressure is essentially composed of the partial pressures of the ammonia, the diluent used and the hydrogen. Since the partial pressure of the ammonia is very high at the reaction temperatures, the ammonia is preferably initially charged with the diluent, whereby a lowering of the total pressure is achieved.

Under these reaction conditions, a liquid and a gaseous phase are formed in the reaction vessel.

The ammonia is used in a high, molar excess based on the aldehyde. At least 15, preferably from 20 to 50, very preferably from 20 to 35, mol of ammonia are used per mol of aldehyde. Hydrogenation catalysts used are conventional catalysts used for the reductive amination of carbonyl compounds, such as nickel, cobalt, platinum or palladium catalysts or compounds of such metals, for example oxides, which may be alloyed, interspersed or coated with one another and/or with other metals or metal compounds, for example iron, rhodium or copper. The catalyst can here be used as such, applied to a conventional support, or as fixed bed catalyst or monolithic catalyst. In general, 5.0 g of catalyst are used per mol of aldehyde. However, since the optimum amount of catalyst depends on its effectiveness, it can be advantageous to use larger or smaller amounts of catalyst. The optimum catalyst and the optimum amount of catalyst can easily be determined for each aldehyde by preliminary experiments. When using unsaturated aldehydes, the catalyst used is one which does not attack a C—C multiple bond under the reaction conditions. Such catalysts, such as for example nickel catalysts, are known. The hydrogen is introduced in a customary manner into the reaction mixture, preferably hydrogen pressure is applied over the liquid phase, a hydrogen partial pressure of at least 3 bar, preferably of at least 5 bar, being applied and maintained. Higher hydrogen pressures can here be advantageous.

In carrying out the reduction of the invention, each aldehyde group present in the reaction mixture is converted into an amino group. On the basis of experience with conventional processes, the reaction time required is amazingly short. Completely unexpectedly, the reaction is generally concluded within half an hour and in many cases even after a few minutes.

The reaction can be carried out continuously or batchwise and is preferably carried out continuously.

The end of the reaction, or the residence time in a continuous reaction procedure, is, as is customary, preferably determined by chromatography. After the reaction is complete, the ammonia and the diluent are removed from the reaction mixture after separating off the catalyst. The residue contains the amine formed from the aldehyde in high purity and in yields which are usually far above 90%. Optionally, a further purification step, for example by chromatography or distillation, can be appended. Amines which cannot be distilled can also be purified further by conversion into one of their salts, for example into the hydrochloride, hydrosulfate or acetate.

BRIEF DESCRIPTION OF DRAWING

The invention further provides an apparatus for carrying out the process, as set forth in the diagram. In the diagram, A is a coolable device for feeding in the aldehyde which is to be reacted, S is a coolable device for conveying the diluent, M is a mixing vessel which can be cooled, RC is the reaction vessel which is pressure-tight, can be heated and contains a mixing device ST and the catalyst C and also feed lines for hydrogen $H_2$, ammonia $NH_3$, the diluent S and the aldehyde A and a discharge facility for the fully reacted mixture RM which comprises the product, ammonia and optionally hydrogen and diluent. D is a workup facility, preferably a distillation facility, in which the volatile ammonia and optionally hydrogen are removed from the fully reacted mixture, the diluent is evaporated and the product is isolated.

For carrying out the reaction, the aldehyde A is dissolved in the diluent S in the mixing vessel M in such a way that the temperature of the solution does not exceed 5° C. The reaction vessel RC is initially charged with the ammonia $NH_3$, hydrogen $H_2$ and a nickel catalyst at temperatures of from 80° to 150° C. and a pressure of from 20 to 60 bar. Under these conditions there are formed a gaseous phase g and a liquid phase 1. If the ammonia pressure becomes too high, diluent can be added. Since the ammonia dissolves at least partially in the diluent or becomes mixed therewith, the total pressure is reduced in this way. The solution of the aldehyde in the diluent used is introduced into this liquid phase 1. The mixing through of the liquid and gaseous phases is carried out by a mixing device, for example by an agitator; the reaction generally occurs practically instantaneously and generally only very short residence times of the reactants in the reaction vessel are required. Less reactive aldehydes require a longer residence time. The reaction time, i.e. the optimum residence time, namely the feed rate of the reactants and the discharge rate of the fully reacted mixture, can be determined without difficulty for each aldehyde by preliminary experiments. The fully reacted reaction mixture RM is discharged, a simultaneous, undesired discharge of the catalyst C being prevented, for example by use of a frit. The reaction mixture RM can then be fed to a distillation facility D in which the ammonia and optionally the hydrogen and the diluent are separated off from the product and recirculated to the reaction vessel, with the diluent being optionally subjected beforehand to purification, for example for removal of the reaction water formed, or the fully reacted reaction mixture RM being worked up in a conventional manner after discharge independently of the apparatus. It has been found that a pulsating, continuous change of the aldehyde concentration in the reaction mixture can be advantageous for optimum conversion. It is therefore preferred that at certain time intervals, which can easily be determined from case to case, only diluent instead of the mixture of aldehyde/diluent is introduced into the reaction vessel and the addition of aldehyde is briefly interrupted.

In the manner described, very pure primary amines are prepared in high yields and in extremely short reaction times. The invention accordingly constitutes an advance in the art.

EXAMPLE 1

215.6 g of ammonia (12.65 mol), 150 ml of methanol and 5 g of nickel catalyst Ni 5256 from Engelhard containing about 55–60% of nickel on $SiO_2/Al_2O_3$ are introduced into a 2 l pressure vessel and heated to a temperature of 110° C. After pressurizing with hydrogen, a total pressure of 58 bar was set. A liquid and a gaseous phase were formed. 6.77 g of 1,8-octanedialdehyde having a purity of 97.3% were dissolved in 50 ml of methanol at temperatures of from −5° to 0° C. This solution, which was maintained at a temperature of about 0° C., was introduced over a period of 25 minutes into the stirred, liquid phase in the pressure reactor. Consumption of hydrogen, which was measured, ceased about 5 minutes after introduction of the solution was complete, and the reaction mixture was taken from the reactor via a frit which retained the catalyst. The ammonia was evaporated from the reaction mixture and the methanol and the water of reaction formed were distilled off. The residue of 7.4 g was distilled in a bubble tube, giving 6.42 g of 1,8-octanediamine having a purity of 99%, i.e. 95% of theory based on pure aldehyde.

EXAMPLE 2 was carried out as described in Example 1, but continuously. After initially charging ammonia, catalyst suspension and hydrogen, 1440 ml/hour of ammonia, 800 ml/hour of methanol and 28.4 ml/hour of 1,8-octanedialdehyde were introduced into the liquid phase of the pressure reactor, a total pressure of 58 bar being maintained by feeding in hydrogen. 2228.4 ml/h of reaction solution were simultaneously discharged from the reactor. Discharge was carried out by taking out about 557 ml of reaction solution after every 25 minutes. Each fraction was separately worked up. The results summarized in Table 1 were obtained:

TABLE 1

| Cycle | Evaporation residue in gram | Diamine in gram | Yield % of theory |
|---|---|---|---|
| 1 | 5.3 | 4.9 | 71.4 |
| 2 | 7.4 | 6.2 | 90.8 |
| 3 | 8.9 | 7.3 | 106.4 |
| 4 | 3.2 | 1.4 | 20.4 |
| 5 | 3.4 | 0.8 | 11.7 |
| Total | 28.2 | 20.6 | 60.1 |

EXAMPLE 3 was carried out as described in Example 2, but after charging the pressure reactor with ammonia, catalyst and hydrogen, 2500 ml of ammonia/h, 1500 ml/h of methanol and 83.8 ml/h of 1,8-octanedialdehyde were introduced into the liquid phase of the pressure reactor. After every 24 minutes the feeding in of the 1,8-octanedialdehyde was stopped and each time both 500 ml of ammonia and 150 ml of methanol were introduced for 12 minutes. At the same time, 2283.5 ml of the reaction mixture were continuously taken out of the reactor every 36 minutes, this material being separately worked up in each case. The results summarized in Table 2 were obtained:

TABLE 2

| Cycle | Evaporation residue in gram | Diamine in gram | Yield % of theory |
|---|---|---|---|
| 1 | 34.3 | 30.3 | 93.5 |
| 2 | 35.7 | 29.4 | 90.8 |
| 3 | 33.2 | 30.4 | 93.8 |
| 4 | 35.1 | 29.7 | 91.7 |
| 5 | 32.5 | 30.0 | 92.6 |
| Total | 170.8 | 149.8 | 92.4 |

EXAMPLES 4 AND 5 were carried out in the manner described in Example 1, but using 150 ml of toluene and 150 ml of methyl tert.-butyl ether respectively instead of 150 ml of methanol in the pressure reactor and 50 ml of toluene and 50 ml of methyl tert.-butyl ether respectively instead of 50 ml of methanol as solvent for the 1,8-octanedialdehyde, giving a yield of 1,8-octanediamine of 90.1 and 87.8% respectively of theory.

EXAMPLE 6 was carried out in the manner described in Example 1, but using 1,12-dodecanedialdehyde having a purity of 98.3% instead of the 1,8-octanedialdehyde. This gave 9.75 g of 1,12-dodecanediamine having a purity of 98%, i.e. a yield of 97% of theory based on the pure aldehyde.

EXAMPLE 7 was carried out as described in Example 3, but feeding in 5000 ml/h of ammonia, 250 g/h of 1,12-dodecanedialdehyde and 5000 ml/h of methanol while at the same time continuously discharging 2050 ml of the reaction mixture every 12 minutes. The average mean residence time of the reactants, i.e. that time in which the reactor volume is practically replaced, was 3.98 minutes. The yield of 1,12-dodecanediamine obtained was over 97%, the purity was about 98%.

EXAMPLES 8 TO 22

Examples 8 to 22 were carried out in the manner described in Example 3, but using various aldehydes A as starting material, various aldehyde concentrations c (mol/l) and various residence times h (in minutes) of the reactants. The results summarized in Table 3 were obtained:

TABLE 3

| Example | A | c | V | h |
|---|---|---|---|---|
| 8 | $CH_3(CH_2)_5CHO$ | 0.35 | MeOH | 25 |
| 9 | $CH_3(CH_2)_6CHO$ | 0.40 | MeOH | 25 |
| 10 | $H_3COOC-(CH_2)_6-CHO$ | 0.80 | MeOH/toluene | 25 |
| 11 | $H_3COOC-(CH_2)_6-CHO$ | 0.80 | pyridine | 25 |
| 12 | $OH-CH_2(CH_2)_6-CHO$ | 0.60 | MeOH | 25 |
| 13 | $(H_3CO)_2-CH-(CH_2)_6-CHO$ | 0.50 | MeOH | 25 |
| 14 | $CH_3(CH_2)_7-CHO$ | 0.60 | MeOH | 11 |
| 15 | $NaOOC-(CH_2)_7-CHO$ | 0.80 | MeOH | 25 |
| 16 | $NaOOC-(CH_2)_{10}-CHO$ | 0.10 | $H_2O$/pyridine | 4 |
| 17 | benzaldehyde | 0.35 | MeOH | 40 |
| 18 | vanillin | 0.15 | MeOH | 60 |
| 19 | piperonal | 0.30 | MeOH | 60 |
| 20 | veratraldehyde | 0.15 | MeOH | 40 |
| 21 | pyridin-2-al | 0.50 | MeOH | 11 |
| 22 | pyridin-4-al | 0.25 | MeOH | 60 |

After workup, the amines and diamines corresponding to the aldehydes and the dialdehydes were obtained in a purity practically equivalent to the aldehyde used as starting material (100% of pure aldehyde gave practically 100% of pure amine) and in yields of over 90% in each case.

The purity of the amines and diamines was determined by gas chromatography via comparison with chemically pure substances.

What we claim is:

1. Process for preparing primary amines from aldehydes in the presence of a diluent, ammonia, using at least 15 mol of ammonia per mol of aldehyde group, a hydrogenation catalyst, hydrogen and isolating the amine formed from the reaction mixture, wherein an aldehyde is mixed with a diluent, where in the case of an alcohol or of water as diluent the mixing temperature is at most 5° C., so that no hemiacetal or aldehyde hydrate is formed and directly afterwards the mixture is practically simultaneously brought into contact with ammonia, hydrogen and the hydrogenation catalyst at temperatures of from 60° to 180° C. and pressures of from 20 to 60 bar.

2. Process according to claim 1, wherein the diluent used is an alcohol having from 1 to 8 carbon atoms.

3. Process according to claim 1, wherein the mixing temperature of the aldehyde and the alcohol or of the aldehyde and the water is from −5° to 0° C.

4. Process according to claim 1, wherein the aldehyde used is an alkanal, alkenal, alkanedial or alkenedial having from 4 to 22 carbon atoms or a benzaldehyde which may be unsubstituted or substituted by hydroxyl or alkoxy groups having from 1 to 6 carbon atoms, a pyrrole aldehyde or a pyridine aldehyde.

5. Process according to claim 1, wherein a reaction temperature of from 80° to 130° C. is maintained.

6. Process according to claim 1, wherein the hydrogenation catalyst used is a nickel catalyst.

7. Process according to claim 1, wherein the reaction is carried out under a pressure of from 40 to 60 bar.

8. Process according to claim 1, wherein a mixing vessel M which can be cooled and is provided with a feed facility for an aldehyde A and a diluent S and a discharge facility for the diluent or the mixture of aldehyde and diluent, is connected by means of a line to a reaction vessel RC which is pressure tight and heatable and is provided with a mixing device ST and feed lines for ammonia $NH_3$ and hydrogen $H_2$, with the reaction vessel being provided with a discharge facility for the fully reacted reaction mixture RM which prevents discharge of the catalyst C and with the reaction vessel RC being optionally connected by means of a line to a distillation facility D in which the amine formed in the reaction vessel can be separated from ammonia, optionally hydrogen and the diluent S, with the distillation facility D being connected by means of a line, in which the separated ammonia and hydrogen can be conveyed, to the reaction vessel RC and by means of a line in which the separated, optionally purified diluent can be conveyed, to the mixing vessel M, is used.

9. Process according to claim 8, wherein the concentration of the aldehyde in the reaction vessel RC is continuously changed by briefly stopping the aldehyde feed and introducing pure diluent and optionally ammonia.

* * * * *